(12) United States Patent
Feye

(10) Patent No.: US 7,022,518 B1
(45) Date of Patent: Apr. 4, 2006

(54) APPARATUS AND METHOD FOR CO-CULTURING OF CELLS

(76) Inventor: Glen Feye, 1340 W. Pennsylvania Ave., San Diego, CA (US) 92103

( * ) Notice: Subject to any disclaimer, the term of this patent is extended or adjusted under 35 U.S.C. 154(b) by 0 days.

(21) Appl. No.: 11/045,334

(22) Filed: Jan. 31, 2005

(51) Int. Cl.
*C12M 1/12* (2006.01)

(52) U.S. Cl. ............................... 435/297.1; 435/297.4; 435/299.2

(58) Field of Classification Search ............. None
See application file for complete search history.

(56) References Cited

U.S. PATENT DOCUMENTS

| | | | |
|---|---|---|---|
| 3,647,632 A | | 3/1972 | Johnson et al. |
| 4,238,568 A | | 12/1980 | Lynn |
| 4,317,886 A | | 3/1982 | Johnson et al. |
| 4,912,048 A | | 3/1990 | Smith et al. |
| 4,912,058 A | | 3/1990 | Mussi et al. |
| 5,010,013 A | | 4/1991 | Serkes et al. |
| 5,026,650 A | | 6/1991 | Schwarz et al. |
| 5,426,037 A | * | 6/1995 | Pannell et al. ............ 435/70.21 |
| 5,449,617 A | | 9/1995 | Falkenberg et al. |
| 5,527,705 A | | 6/1996 | Mussi et al. |
| 5,672,505 A | | 9/1997 | Jones et al. |
| 5,843,780 A | | 12/1998 | Thomson |
| 5,866,419 A | | 2/1999 | Meder |
| 6,001,643 A | | 12/1999 | Spaulding |
| 6,150,159 A | | 11/2000 | Fry |
| D482,795 S | | 11/2003 | Whitley |
| 2002/0086418 A1 | | 7/2002 | Powell |
| 2002/0155594 A1 | | 10/2002 | Hsieh et al. |
| 2004/0029264 A1 | | 2/2004 | Robbins, Jr. |
| 2004/0101955 A1 | | 5/2004 | Whitley |
| 2004/0191895 A1 | | 9/2004 | Whitley |

FOREIGN PATENT DOCUMENTS

WO  WO 02/079497  3/2002

OTHER PUBLICATIONS

Kehat et al., "Human embryonic stem cells can differentiate into myocytes with structural and functional properties of cardiomyocytes," J. Clin. Invest., vol. 108(3), Aug. 2001, pp. 407-414.

Timmermans et al., "Stem Cells for the Heart, Are We There Yet?," Cardiology, vol. 100, 2003, pp. 176-185.

Haider et al., Myoblast Transplantation for Cardiac Repair: A Clinical Perspective, Molecular Therapy, vol. 9, No. 1, Jan. 2004, pp. 14-23.

Zandstra et al., "Scalable Production of Embryonic Stem Cell-Derived Cardiomyocytes," Tissue Engineering, vol. 9, No. 4, 2003, pp. 767-778.

Grounds et al., "The Role of Stem Cells in Skeletal and Cardiac Muscle Repair," The Journal of Histochemistry & Cytochemistry, vol. 50 (5), 2002, pp. 589-610.

Gardner et al., "Culture and transfer of human blastocysts increases implantation rates and reduces the need for multiple embryo transfers," Fertility and Sterility, Abstract, vol. 69, Issue 1, Jan. 1998, pp. 84-88.

Thomson et al., "Embryonic Stem Cell Lines Derived from Human Blastocysts," Science, vol. 282, No. 5391 Issue, Nov. 1998, pp. 1145-1147.

Wobus et al., "Pluripotent mouse embryonic stem cells are able to differentiate into cardiomyocytes expressing chronotropic responses to adrenergic and chclinergic agents and Ca2+ channel blockers," Differentiation, Abstract, vol. 48 (3), 1991, pp. 173-182.

Bongso et al., "Improved quality of human embryos when co-cultured with human ampullary cells," Hum. Reprod., Abstract, vol. 4 (6), Aug. 1989, pp. 706-713.

\* cited by examiner

*Primary Examiner*—James Ketter
(74) *Attorney, Agent, or Firm*—Christopher Wood

(57) ABSTRACT

A co-culture apparatus and method for, among other things, converting a progenitor cell line into a target cell line. The apparatus comprises an exterior receptacle, a removable cartridge that fits into the exterior receptacle, and a closure member to seal the apparatus. The invention is also directed to a method for transforming a progenitor cell line into a target cell line. In one embodiment of the invention, the method comprises the steps of: establishing a progenitor cell line; establishing a support cell line; co-culturing said progenitor and support cell lines; establishing a transformation cell line; and co-culturing said progenitor and transformation cell lines, wherein the transformation cell line supports the transformation of the progenitor cell line into a target cell line.

10 Claims, 14 Drawing Sheets

APPARATUS AND METHOD FOR CO-CULTURING OF CELLS

CROSS-REFERENCE TO RELATED APPLICATIONS

Not Applicable.

STATEMENT REGARDING FEDERALLY SPONSORED RESEARCH OR DEVELOPMENT

Not Applicable.

SEQUENCE LISTING

Not Applicable.

FIELD OF THE INVENTION

The present invention relates generally to co-culturing of cells and more particularly to an apparatus and method for trans-membrane co-culturing of different cell types such as different species of microorganisms, different cell lines derived from human tissue, or different cell lines derived from animal tissue.

BACKGROUND OF THE INVENTION

U.S. Pat. No. 3,647,632, issued Mar. 7, 1972 to Johnson et al., describes a method and apparatus for growing cells such as microorganisms or cells derived from the tissues or living organisms. The Johnson '632 apparatus enabled the continuous growth of cells in a liquid media suspension. The '632 apparatus could be used in a steady state mode in which cells are drawn off to maintain a constant population of cells or to grow higher concentrations of cells than that normally possible with typical batch cultures.

The Johnson '632 invention was not suitable for growing human and animal cell cultures as monolayer cultures on an artificial solid substrate. In vitro monocultures of cell lines are typically performed in culture vessels such as dishes, flasks and multiwell plates that provided the surfaces upon which the cell monolayer formed.

More recently, roller bottles have been used to grow and harvest animal or human cell cultures such as those manufactured by Becton, Dickinson and Company of Franklin Lakes, N.J.; e.g., see U.S. Pat. No. 5,010,013 issued Apr. 23, 1991 Serkes et al., which describes a roller bottle for cell growth. The Serkes et al. '013 roller bottle contains a wall formed of a plurality of corrugations; in one embodiment the corrugations are symmetrical and perpendicular to the axis of the bottle, and have at least one drain channel formed by at least one and preferably two opposed flat axial, uncorrugated panels and optionally containing axial reinforcement ribs provided along the outer edge of the corrugations. The corrugations are discontinuous along the inside surface of the panels to form drainage channels. The surface area of the bottle is 110 to 500% larger than an uncorrugated bottle having the same exterior dimensions. The Serkes et al. '013 roller bottle is not suitable for co-culturing of different cell lines such as different human cell lines.

U.S. Pat. No. 5,527,705, issued Jun. 18, 1996 to Mussi et al., describes a roller bottle for trans-membrane co-culture of cells. The Mussi '705 roller bottle includes an exterior receptacle with a longitudinal axis having a first chamber surrounded by a sidewall. The exterior receptacle has a first neck at one end having an opening therethrough providing fluid access to said first chamber. The Mussi '705 roller bottle further includes an interior container with a longitudinal axis and a second chamber, the interior container being located coaxially within the exterior receptacle. The interior container has a second neck at one end providing fluid access to the second chamber. The exterior receptacle is formed from a material that is substantially impermeable to gas and liquid and is sealed in a substantially fluid tight fashion forming the first chamber that has fluid access by the first neck. At least a portion of the interior container is formed from a microporous material. The roller bottle of the invention enables culturing one cell type in the presence of another cell type for the study of interactions between the cells while maintaining a physical separation between the cell types providing a scale up in cell population size from well type inserts. The microporous membrane allows free interchange of media soluble cellular products between the cell types, but maintains physical separation.

Still referring to the Mussi '705 patent, in one embodiment the Mussi '705 roller bottle interior container is removable from the exterior receptacle.

None of the above patents and publications, taken either singularly or in combination, is seen to describe the instant invention as claimed.

SUMMARY OF THE INVENTION

A co-culture apparatus and method for, among other things, converting a progenitor cell line into a target cell line. The apparatus comprises an exterior receptacle, a removable cartridge that fits into the exterior receptacle, and a closure member to seal the apparatus. The invention is also directed to a method for transforming a progenitor cell line into a target cell line. In one embodiment of the invention, the method comprises the steps of: establishing a progenitor cell line; establishing a support cell line; co-culturing said progenitor and support cell lines; establishing a transformation cell line; and co-culturing said progenitor and transformation cell lines, wherein the transformation cell line supports the transformation of the progenitor cell line into a target cell line.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is directed to co-culturing of cells and more particularly to an apparatus and method for trans-membrane co-culturing of different cell types such as different species of microorganisms, different cell populations derived from human tissue, or different cell populations derived from animal tissue.

Referring to the FIGURES in general, the co-culture apparatus of the present invention is indicated generally by the numeral 100; different embodiments of the invention are generally represented by alpha-numeric derivatives of "100", e.g., "100a" and "100b".

Figure 1A:
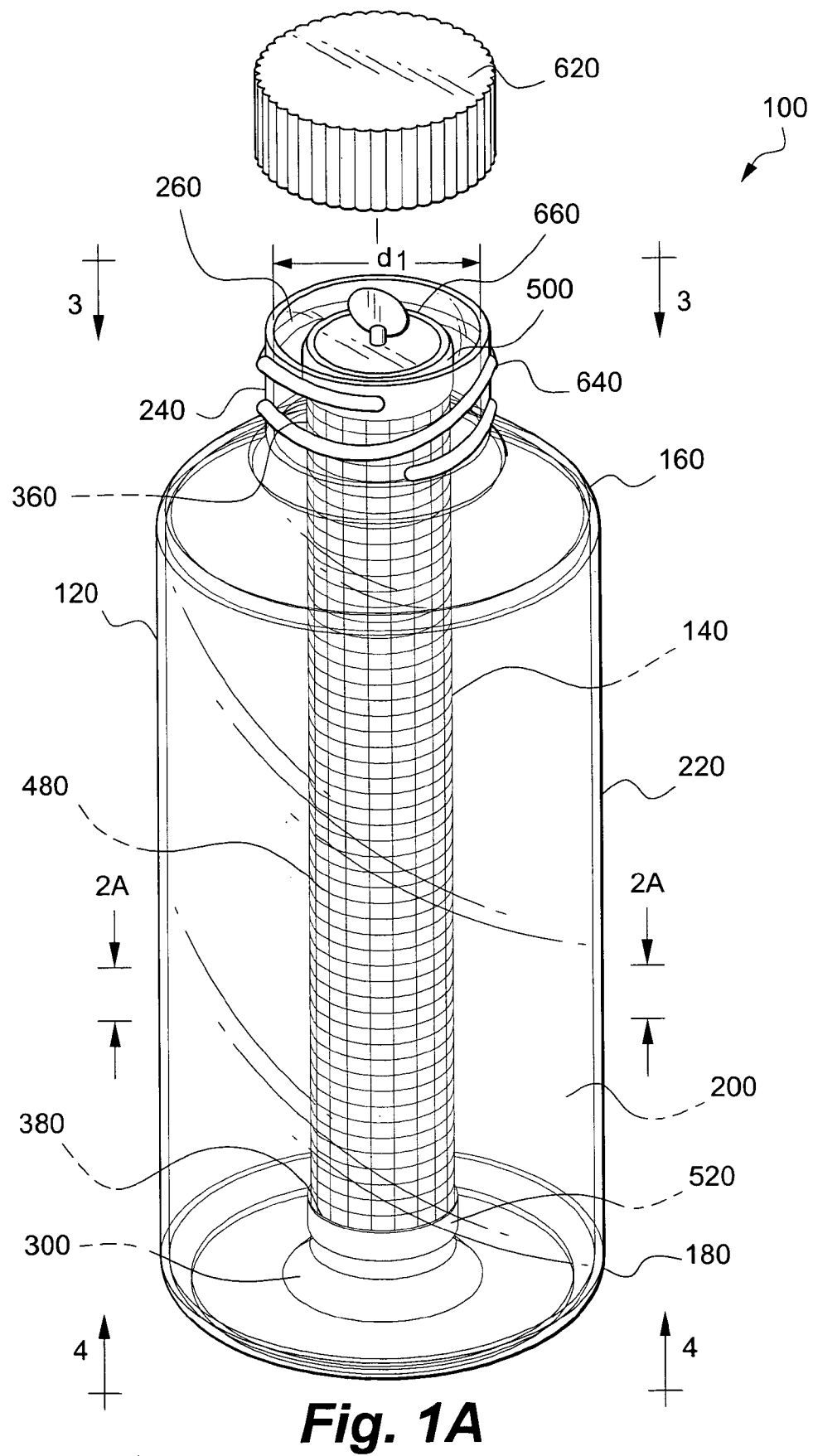
FIG. 1A shows a perspective view of a co-culture apparatus according to one embodiment of the present invention.

Referring to FIG. 1A, the co-culture apparatus 100 includes an exterior receptacle 120 and a removable cartridge 140 both of general cylindrical appearance. During normal use of the co-culture apparatus 100, the cartridge 140 is located coaxially within the exterior receptacle 120. However it should be understood that the overall shape and configuration of the exterior receptacle 120 and/or cartridge 140 may vary; for example, the cartridge 140 can have a non-circular cross-section and have an overall shape akin to an elongated rectangular box.

Figure 2A:
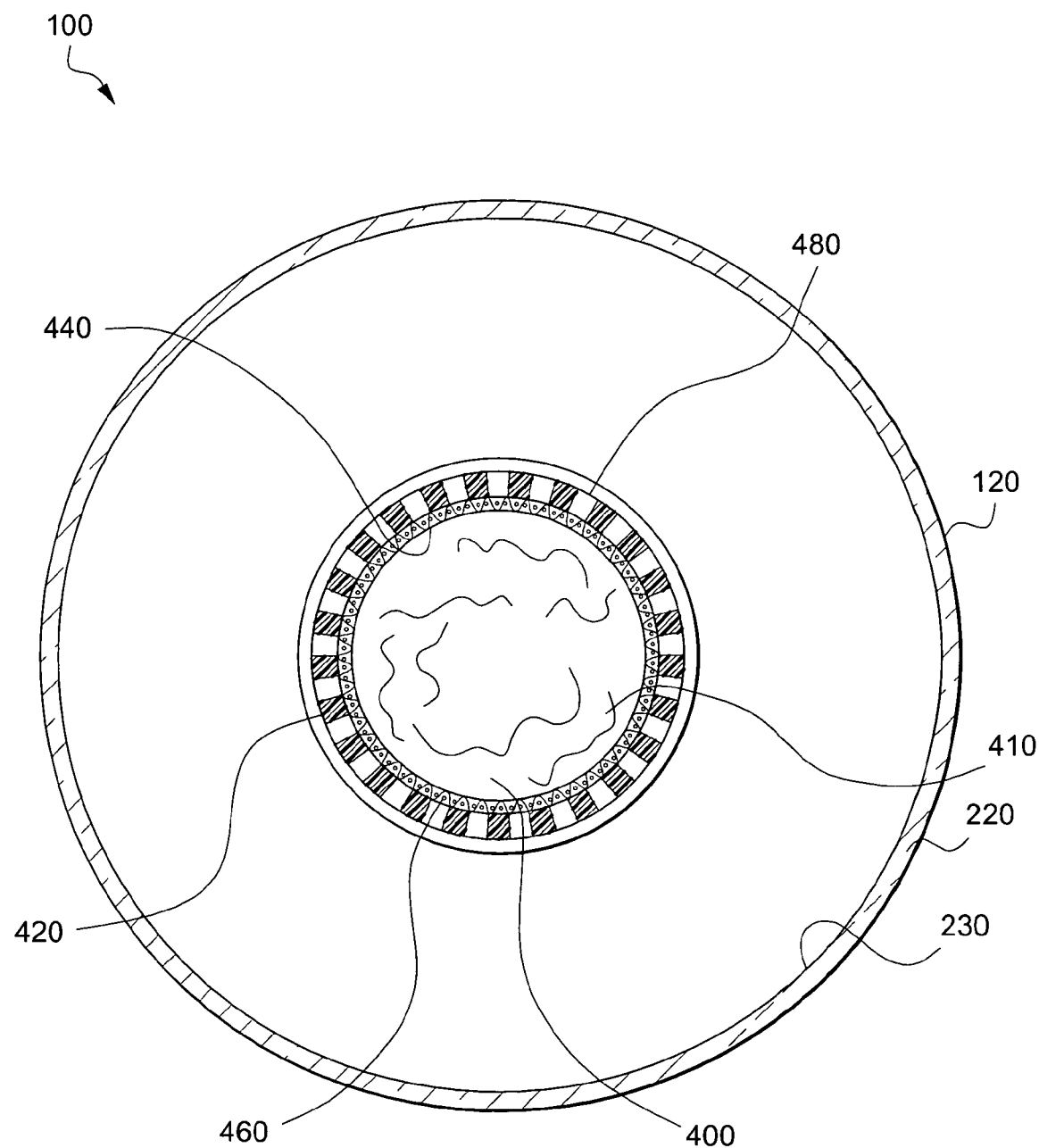
FIG. 2A is section-slice view between lines 2A—2A of the co-culture apparatus of FIG. 1A, wherein the microporous membrane layer 460 is located inside the cartridge sidewall 420.

Referring to FIGS. 1A and 2A, exterior receptacle 120 has first and second opposite ends 160 and 180, and a first chamber 200 surrounded by a first sidewall 220. The first sidewall 220 has a first interior surface 230 (shown in FIG. 2A) to which a first cell population can adhere; the first cell population can comprise of support cells or transformation cells of one or more cell lines to support and/or transform a second population of cells inoculated into cartridge 140.

Opposite end 160 includes a neck 240 with an aperture 260; the aperture 260 has an aperture diameter $d_1$. Second end 180 includes a cartridge-mounting member 300 that faces into the first chamber 200. It should be understood that any suitable cartridge-mounting or attachment device can be used; for example, a circular protruding ring facing into the second chamber 400 and sized to fit around the circumference of second end 380 of cartridge 140 could be used to keep the cartridge 140 centered and in place inside first chamber 200 of exterior receptacle 120.

Figure 1B:
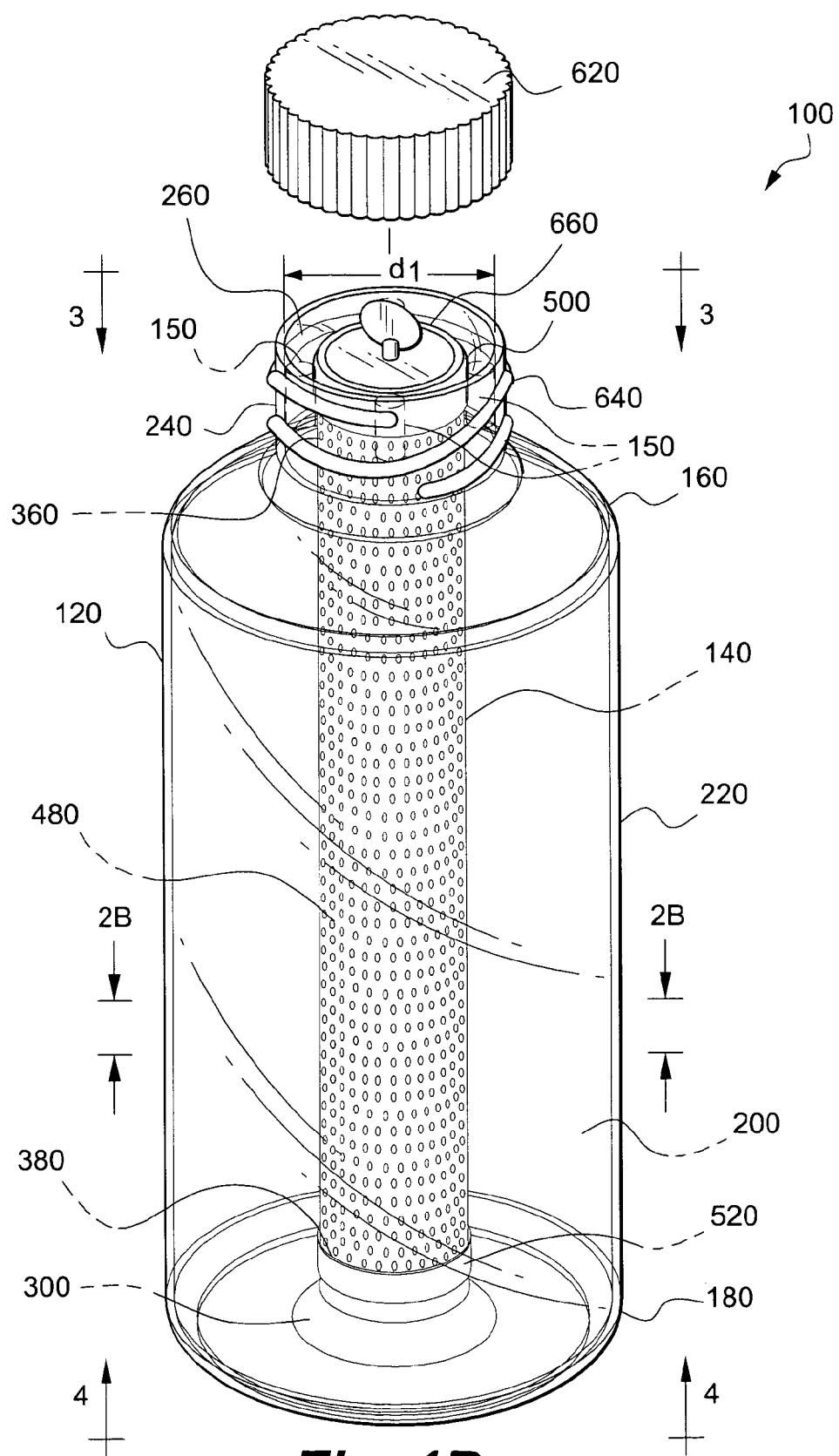
FIG. 1B shows a perspective view of a co-culture apparatus fitted with optional spacers according to another embodiment of the present invention.
Figure 9:
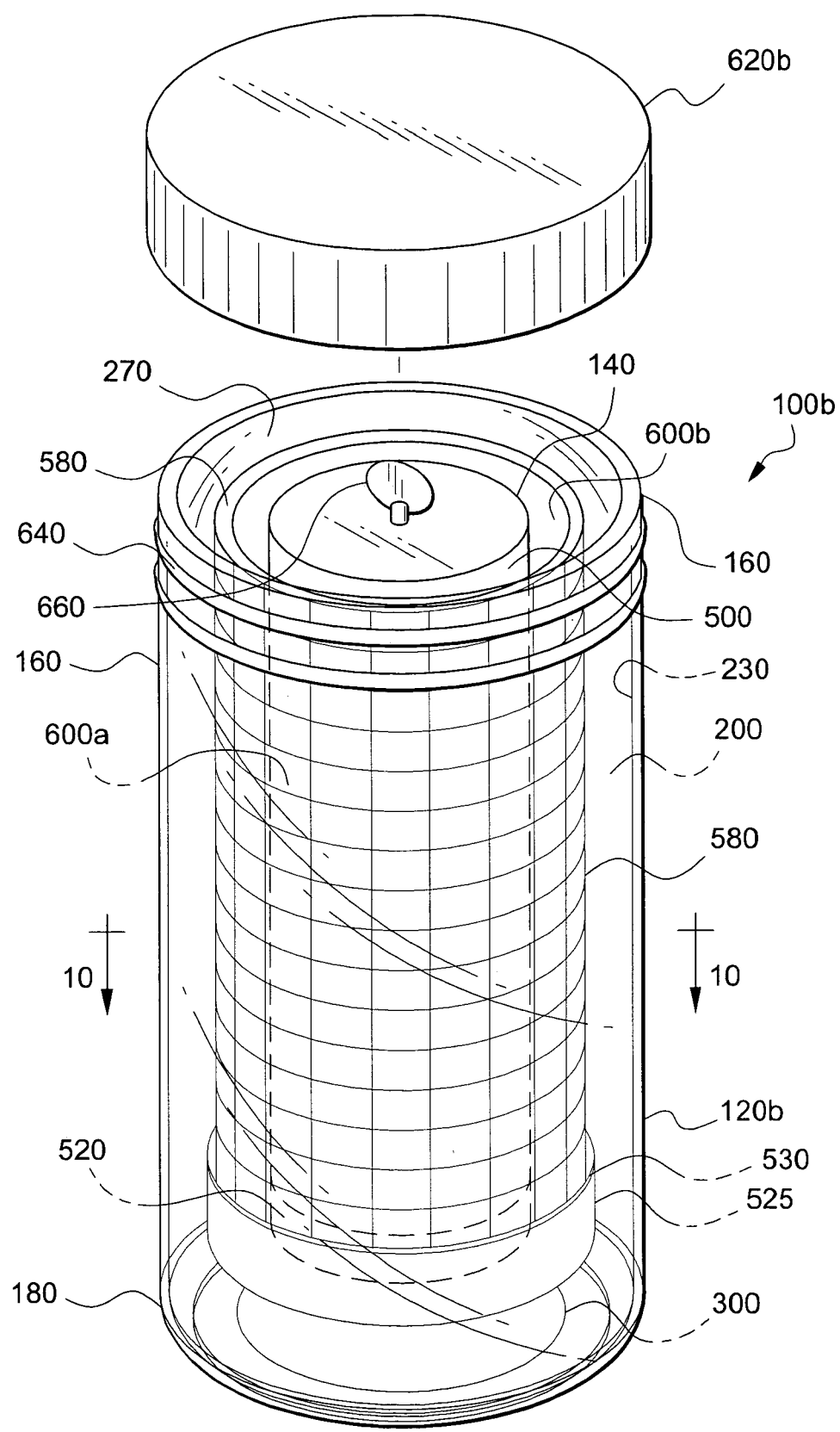
FIG. 9 shows a perspective view of a co-culture apparatus according to a further embodiment of the present invention.

In FIG. 1B, the first end 360 (i.e., top end of cartridge 140) is shown secured inside neck 240 by use of spacers 150; however, the first end 360 of cartridge 140 need not sit inside neck 240 as shown in FIG. 9 where the co-culture apparatus 100 (represented by the alpha-numeral label "100b") lacks neck 240 and cartridge 140 is attached to the bottom 180 of exterior receptacle 120 by means of cartridge-mounting member 300.

A closure member in the form of an internally threaded screw cap 620 is provided to fit over aperture 260 to close or seal the co-culture apparatus 100. The exterior of the neck 240 includes an external thread 640 to reversibly mate with the complementary threaded screw cap 620. The closure member can be any suitable closure or sealing member such as, but not limited to, a snap-on closure member.

Cartridge 140 is normally inserted into the first chamber 200 via neck opening 260; the bottom 380 of the cartridge is reversibly mated to the cartridge-mounting member 300. During normal use of the incubation apparatus 100, first end 360 of cartridge 140 sits inside neck 240. An optional cartridge grip or handle 660 is fitted to first end 360 to facilitate moving the cartridge 140 into and out of the first chamber 200.

Figure 3:
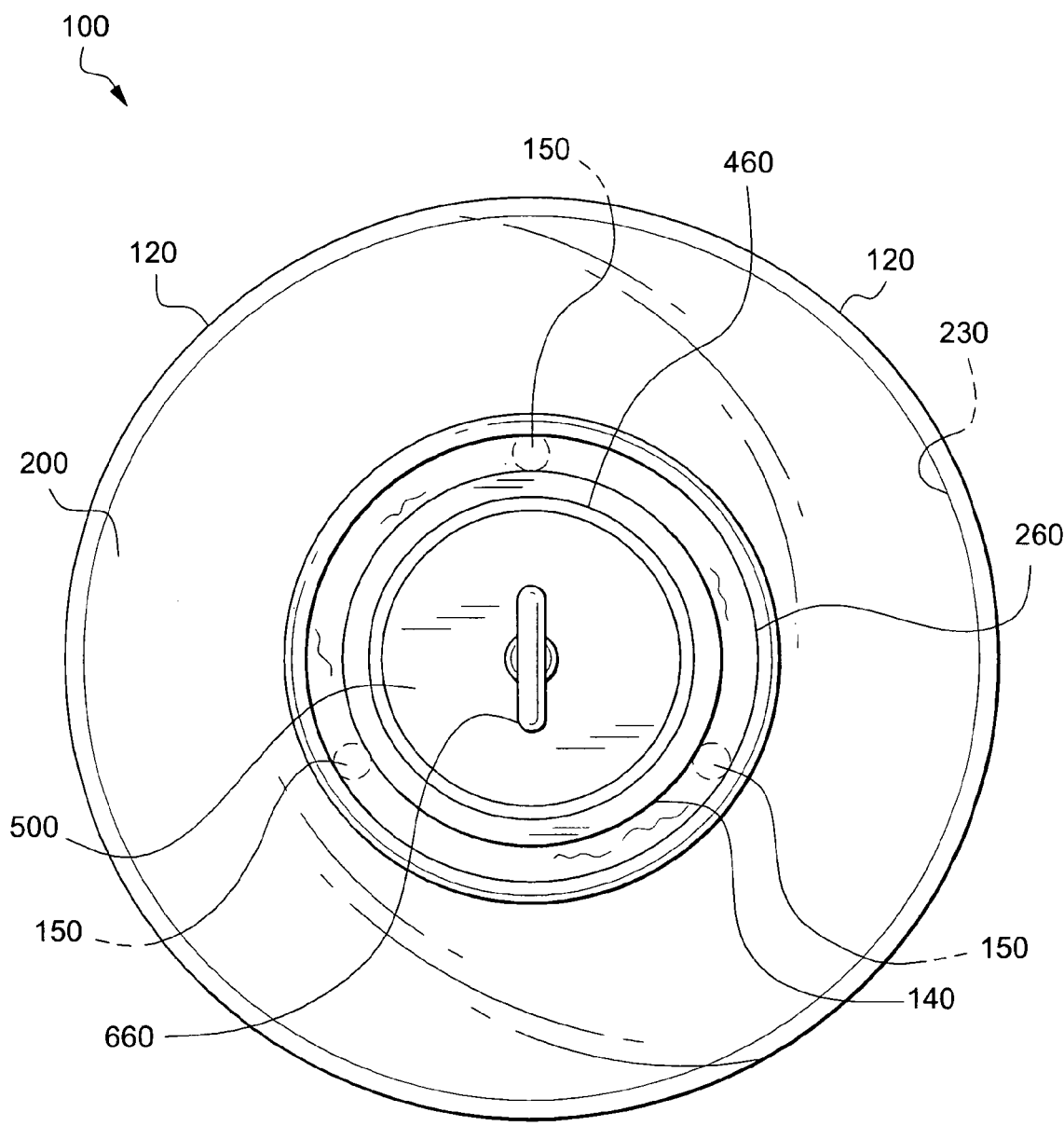
FIG. 3 is a top view of the co-culture apparatus of FIG. 1B.

FIG. 1B shows a perspective view of a co-culture apparatus fitted with one or more optional spacers 150. Optional spacers 150 allow a user or technician to access and add, or replace, growth media in first chamber 200; more specifically, a technician unscrews screw cap 620 and gains access to first chamber 200 between optional spacers 150. The layout of spacers 150 is shown in FIG. 3; however, the layout and number of spacers 150 can vary.

Cartridge 140 has a maximum cartridge diameter $d_2$ that is less than aperture diameter $d_1$. The cartridge 140 has opposite first and second ends 360 and 380, second chamber 400, and a second sidewall 420. The bottom 380 of cartridge 140 is fashioned to fit onto cartridge-mounting member 300.

Cartridge 140 is preferably cylindrical in overall shape with a circular cross-section area (CSA); however, the cartridge 140 can have different configurations and shapes with, for example, an irregular or regular polygonal CSA. If a regular polygonal CSA, the CSA can be, for example, a rectangular, square, pentagonal, hexagonal, or heptagonal CSA.

In one embodiment, second sidewall 420 comprises a layer of microporous material such as a layer of layer of microporous membrane 460 that is selectively permeable, i.e., permeable to cell metabolites in liquid, but substantially prevents direct contact between the support cells (in the first cell line) in the exterior receptacle 120 and the progenitor cells in the second cell line inside the removable cartridge 140. Non-limiting examples of microporous membranes include the track-etched membranes supplied by Cyclopore™ (Avenue Einstein, Louvain-1a-Neuve, Belgium) and Poretics™ (Livermore, Calif.). The second sidewall 420 has a second interior surface 440 to which cells can adhere.

In another embodiment, second sidewall 420 comprises an inner layer of microporous membrane 460 supported and surrounded by a support layer such as a scaffold 480 made of any suitable polymeric material such as a nylon mesh (see FIG. 2A).

Figure 2B:
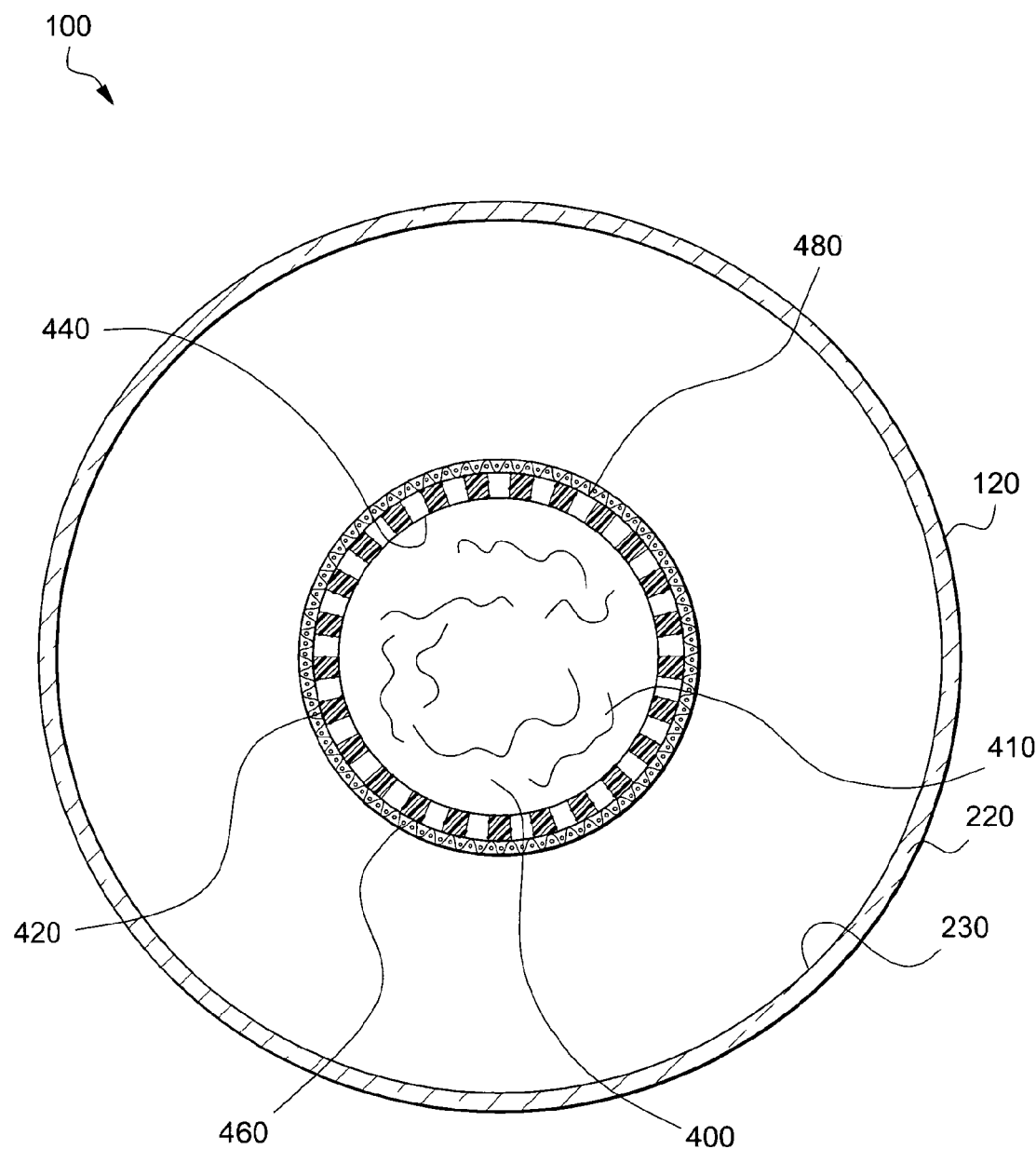
FIG. 2B is an alternative embodiment of FIG. 2A, wherein the microporous layer surrounds the cartridge sidewall 420.

Alternatively, the scaffold 480 is wrapped with microporous material or membrane 460 as shown in FIG. 2B. In this embodiment, the scaffold 480 is wrapped with microporous material or membrane 460 and sealed at both ends with bottom and top caps 500 and 520, respectively.

Figure 2C:
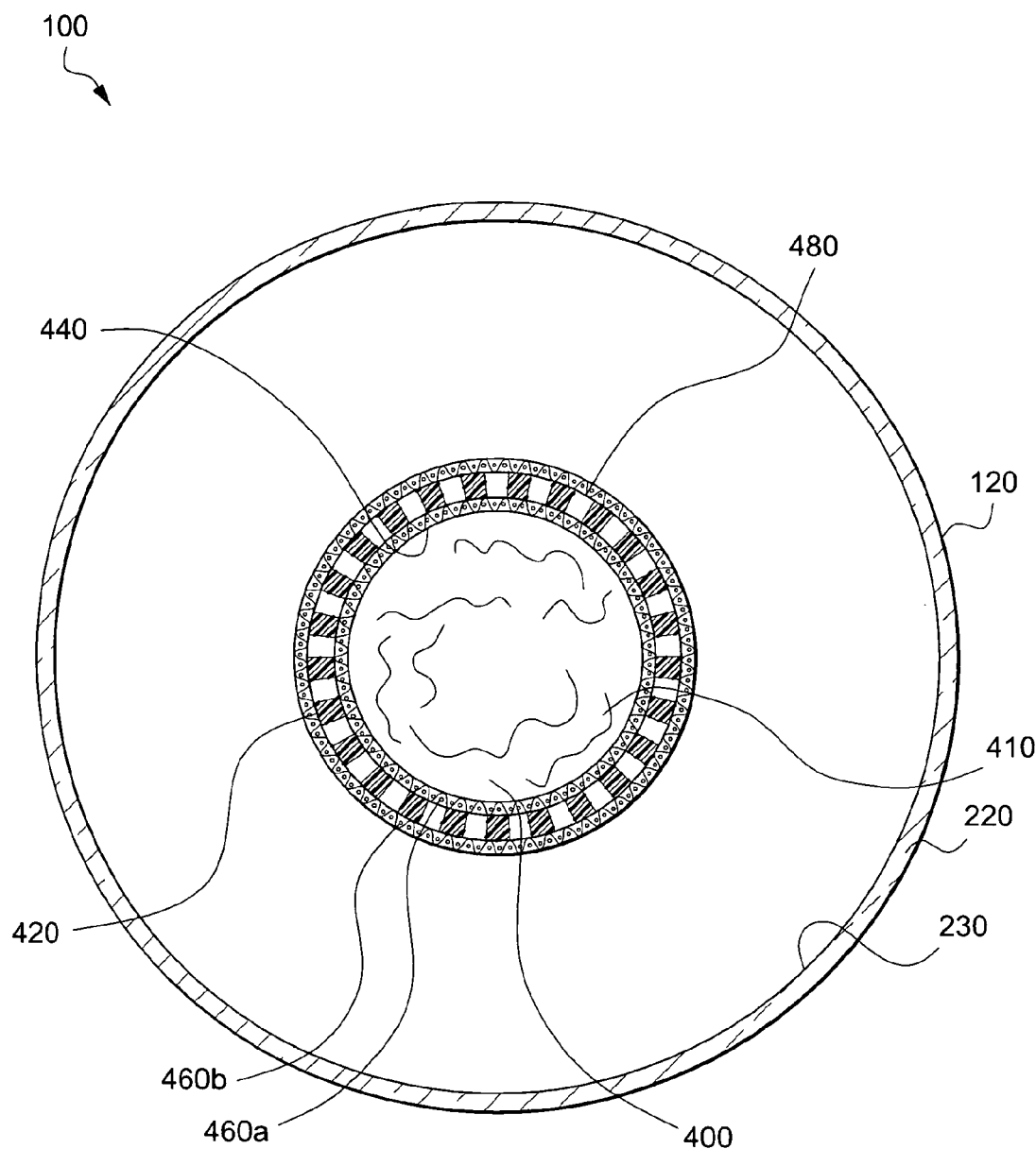
FIG. 2C is a further embodiment of FIG. 2A, wherein the microporous layer comprises inner 460a and outer 460b layers with respect to the cartridge sidewall 420.

FIG. 2C shows a still further embodiment of cartridge 140 (and hence of co-culture apparatus 100) in which the scaffold 480 is wrapped on both sides with microporous membrane 460a and 460b.

In another variation of cartridge 140, at least a portion of the second sidewall 420 is made of a microporous material such as, but not limited to, polyethylene terephthalate, polycarbonate and the like with open pores therethrough of about 10–20 microns in diameter. Such microporous material is described in U.S. Pat. No. 5,527,705 ("the '705 patent"), the '705 patent is herein incorporated by reference in its entirety.

Figure 4A:
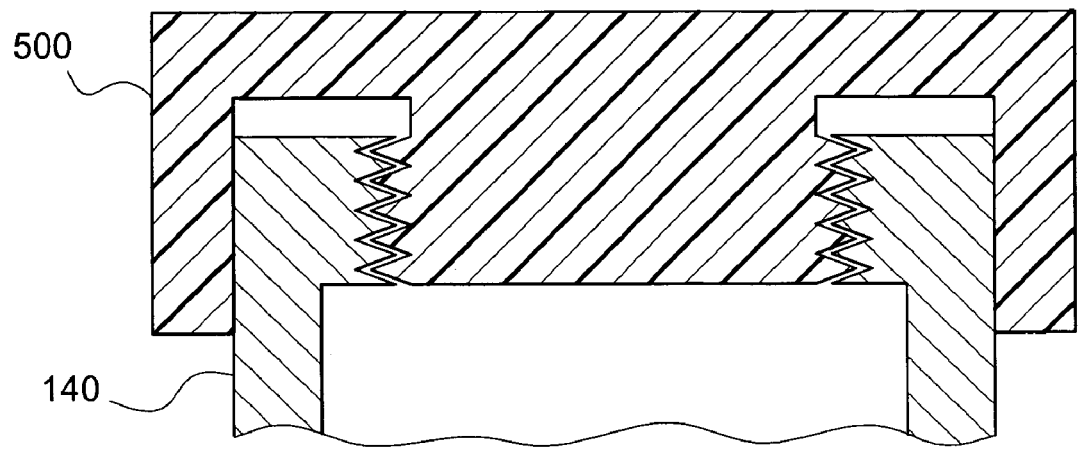
FIG. 4A is a partial side section view of the top part of the cartridge member 140 according to one embodiment of the invention.
Figure 4B:
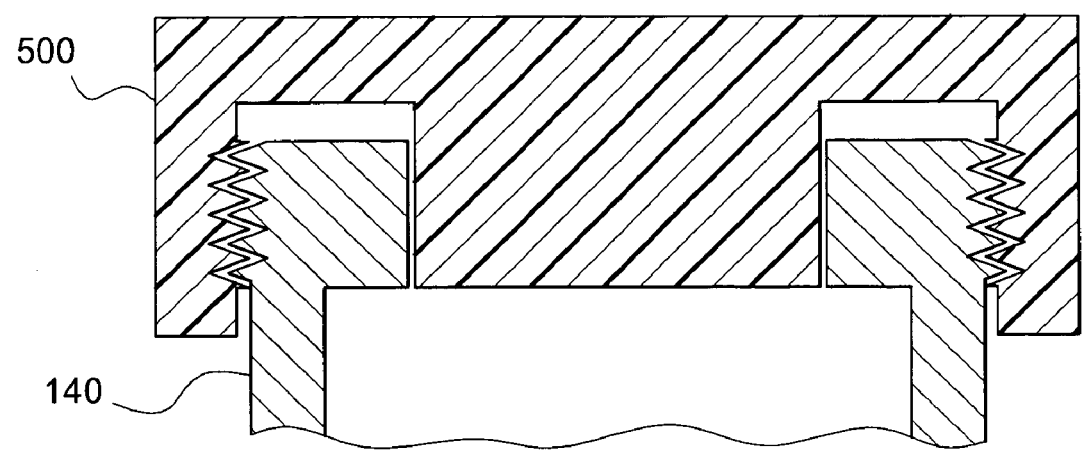
FIG. 4B is a partial side section view of the top part of the cartridge member 140 according to another embodiment of the invention.
Figure 4C:
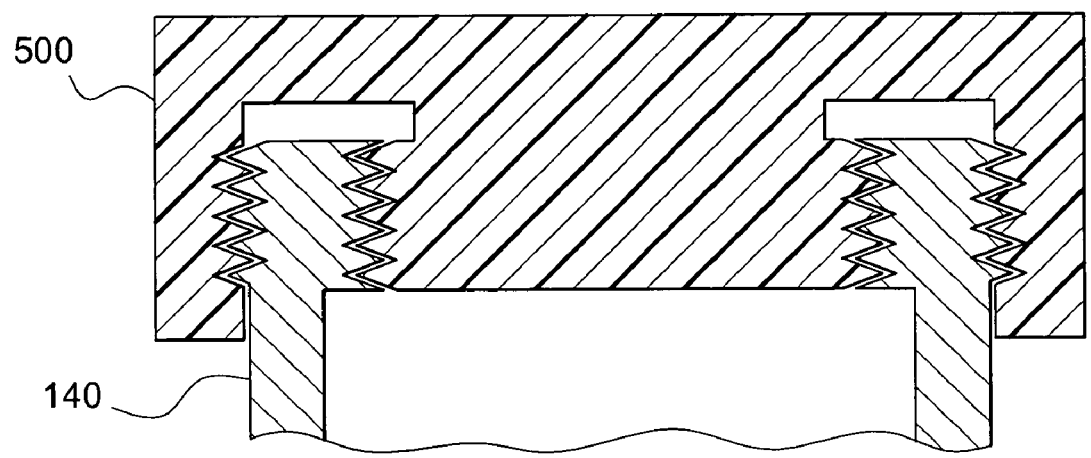
FIG. 4C is a partial side section view of the top part of the cartridge member 140 according to another embodiment of the invention.

Top end 360 of cartridge 140 can be attached to top cap 500 in any suitable manner; non-limiting examples are shown in FIGS. 4A–4C.

Figure 5:
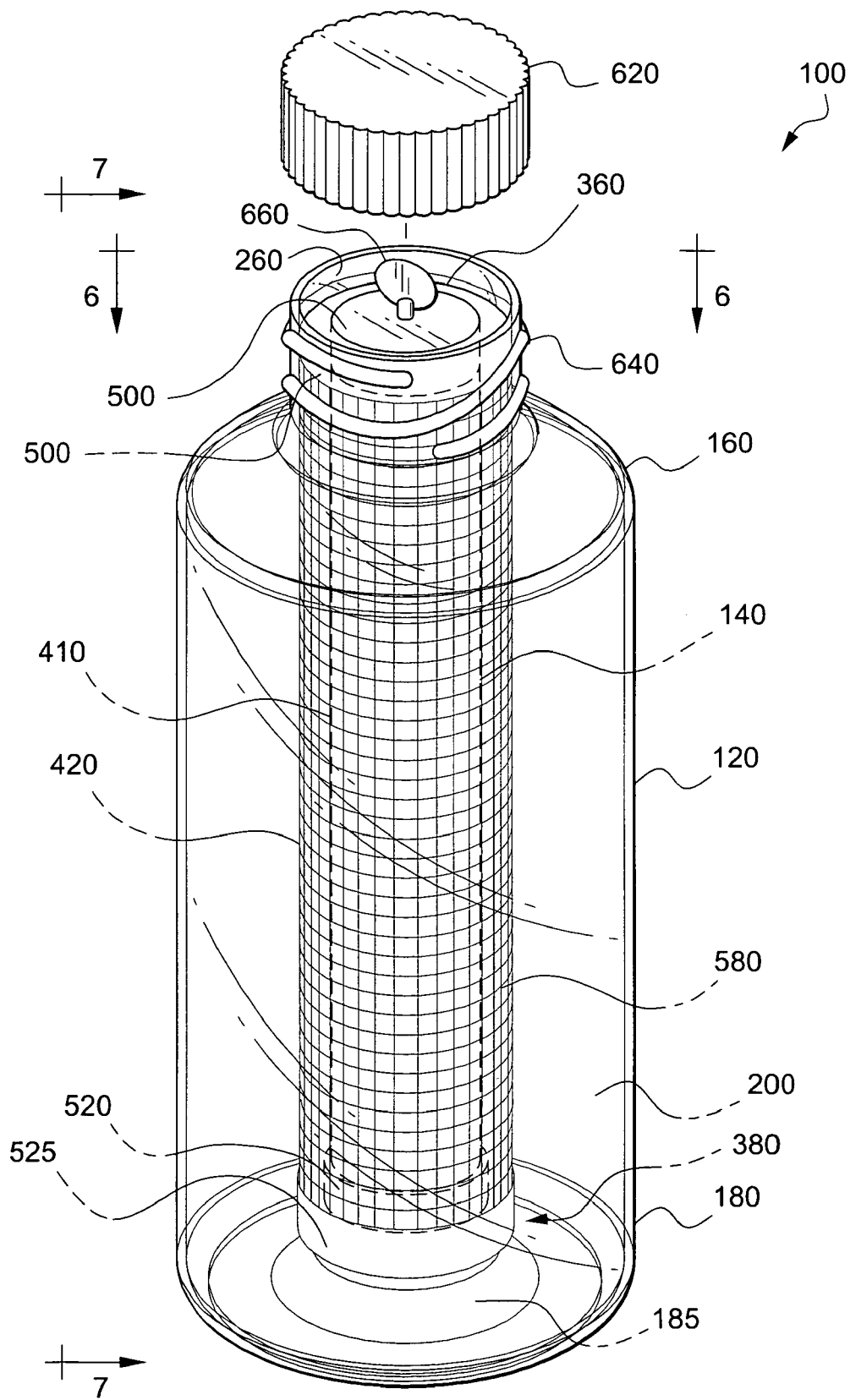
FIG. 5 shows a perspective view of a co-culture apparatus incorporating a sleeve member according to another embodiment of the present invention.

FIG. 5 shows a co-culture apparatus 100 that includes a sleeve member 580. Sleeve 580 is transferred aseptically into the first chamber 200 through aperture 260 and attached to a sleeve holding member 525; sleeve 580 fits around cartridge 140, preferably without touching second sidewall 420. The sleeve 580 provides additional substrate surface area 600 (represented by alpha-numeral labels 600a and 600b for outer and inner surface area, respectively) to allow support and/or transformation cells to adhere and grow thereon. Support and/or transformation cells adhere to the surface 600 and hence grow inside the first chamber 200 but in close proximity to the first cell population inside the cartridge 140 thus facilitating the diffusion of metabolites from the support cells to the progenitor cells in cartridge 140 particularly with respect to progenitor cells adhered to the interior surface 440 of second sidewall 420.

Figure 6:
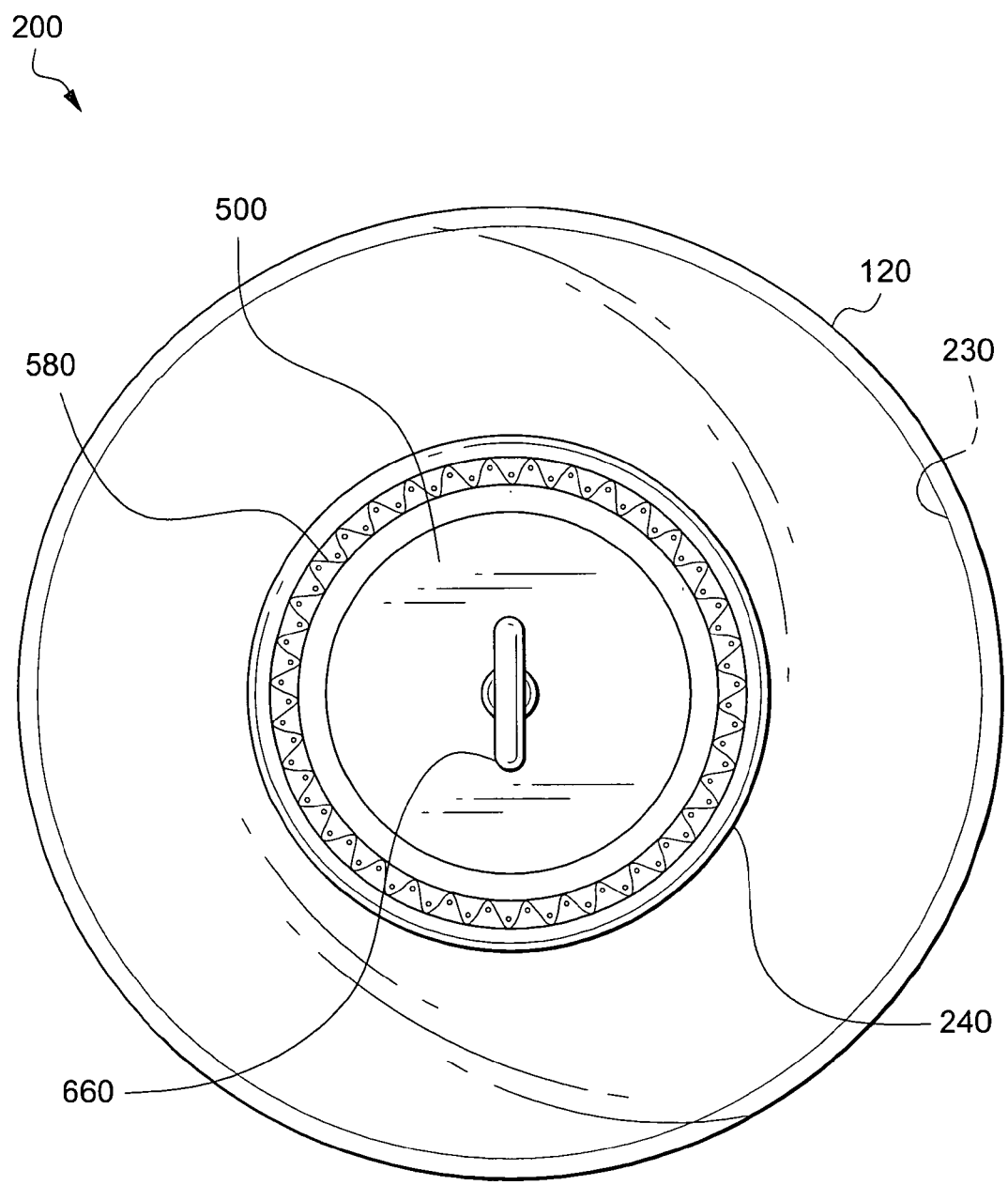
FIG. 6 is a top view between lines 6—6 of the co-culture apparatus of FIG. 5.

Still referring to FIG. 5, the outer diameter of the sleeve 580 is less than the diameter $d_1$ of neck aperture 260. The sleeve 580 can comprise any suitable material such as nylon mesh or polystyrene for supporting the surface growth of the first cell line (or subsequent transformation cell lines on fresh sleeves as described in the methods section below). The sleeve 580 can be coated to promote cell adhesion and growth; for example, the sleeve 580 can be coated with an extracellular matrix component such as collagen and/or fibronectin to induce cellular adherence to the surface of the sleeve 580. FIG. 6 provides a top view between lines 6—6 of the co-culture apparatus of FIG. 5.

Figure 7:
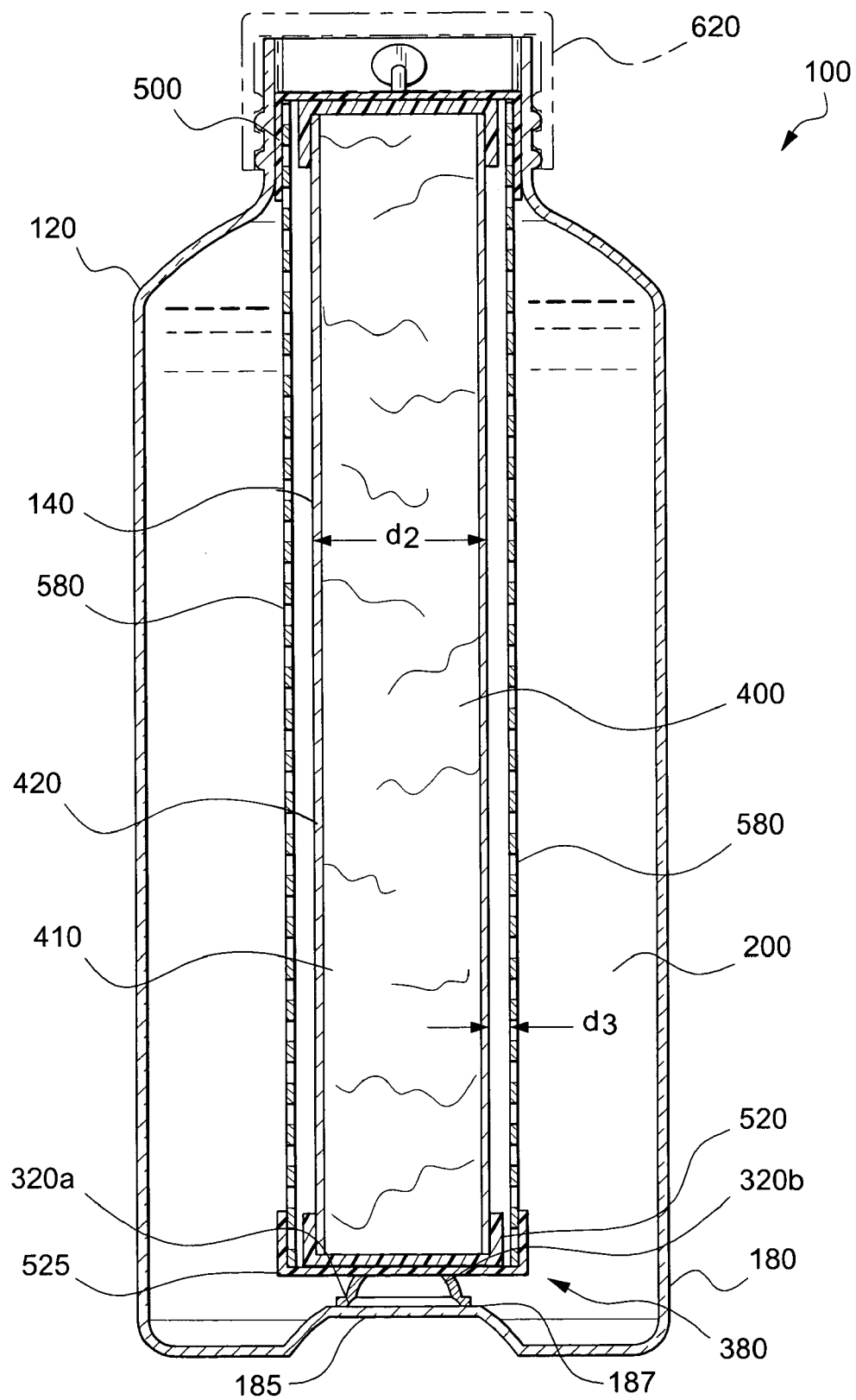
FIG. 7 is a section view taken along lines 7—7 of the co-culture apparatus of FIG. 5.

Still referring to FIG. 5, the bottom 180 of the exterior receptacle 120 includes a recess 185. Recess 185 includes plateau 187, which is shown in section view in FIG. 7, wherein FIG. 7 is a section view taken along lines 7—7 of the co-culture apparatus of FIG. 5. Bottom 380 of cartridge 140 sits on top of the plateau 187. An optional mounting spacer 320a (as shown in FIG. 7) can be used to assist in ensuring a firm contact between bottom 380 of cartridge 140 and plateau 187 of recess 185.

Figure 8:
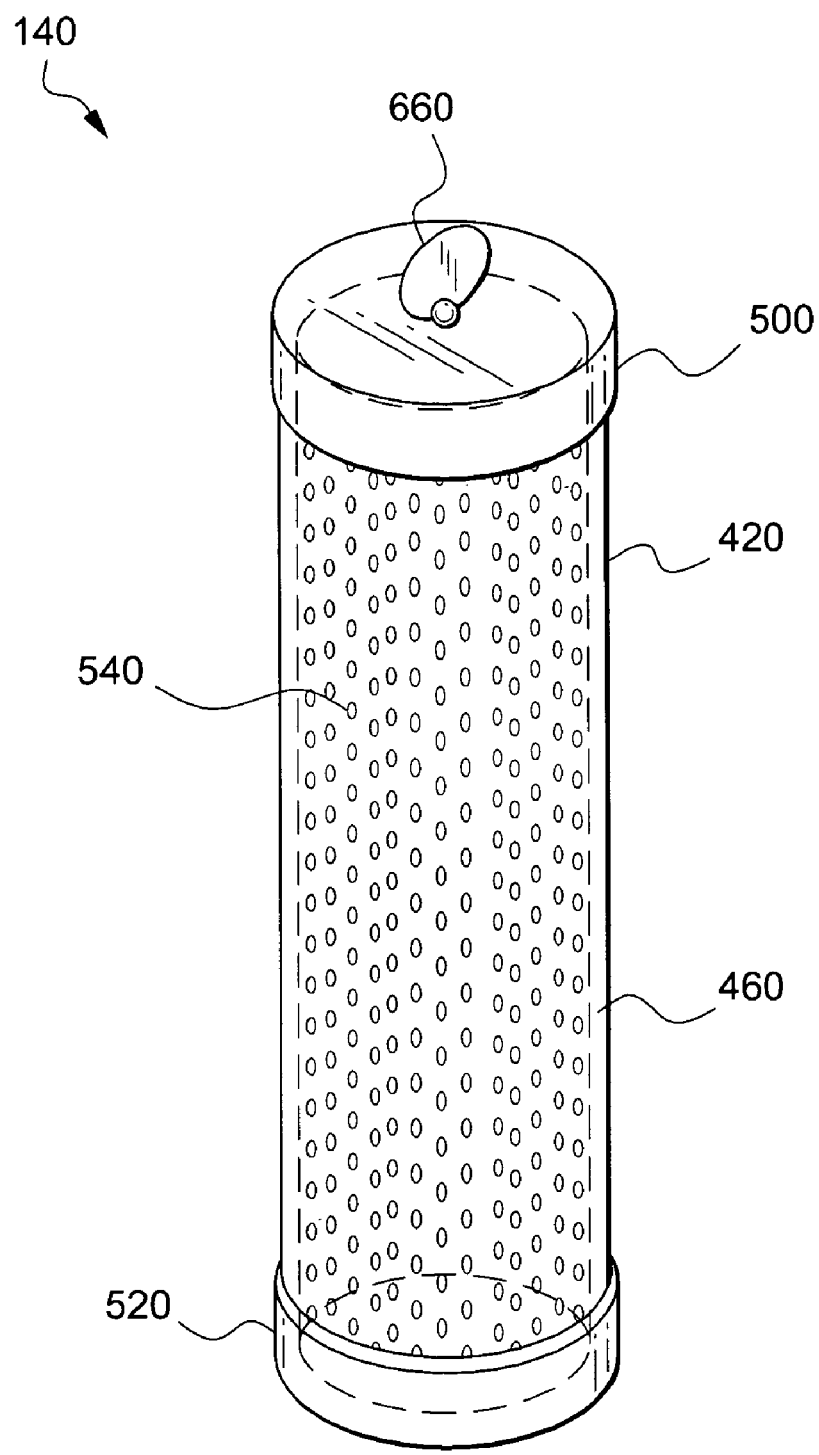
FIG. 8 shows a cartridge member according to an embodiment of the present invention.

FIG. 8 shows another variation of cartridge 140, which comprises a column of perforated polymer 540 with a covering of microporous membrane 460 or polymeric microporous material to provide the second sidewall 420; optional bottom and top caps 500 and 520 help secure the microporous membrane 460 or polymeric microporous material to the column of perforated polymer 540.

Perforated polymer provides more surface area than non-perforated polymer. The column of perforated polymer 540 can be made of perforated polystyrene and/or treated polystyrene such as, but not limited to, oxygen gas plasma treated polystyrene foam that promotes cell attachment as described in U.S. Patent Publication Number 20020155594 A1, published Oct. 24, 2002 to Hsieh et al; the Hsieh et al '594 publication is incorporated herein by reference in its entirety.

Figure 10:
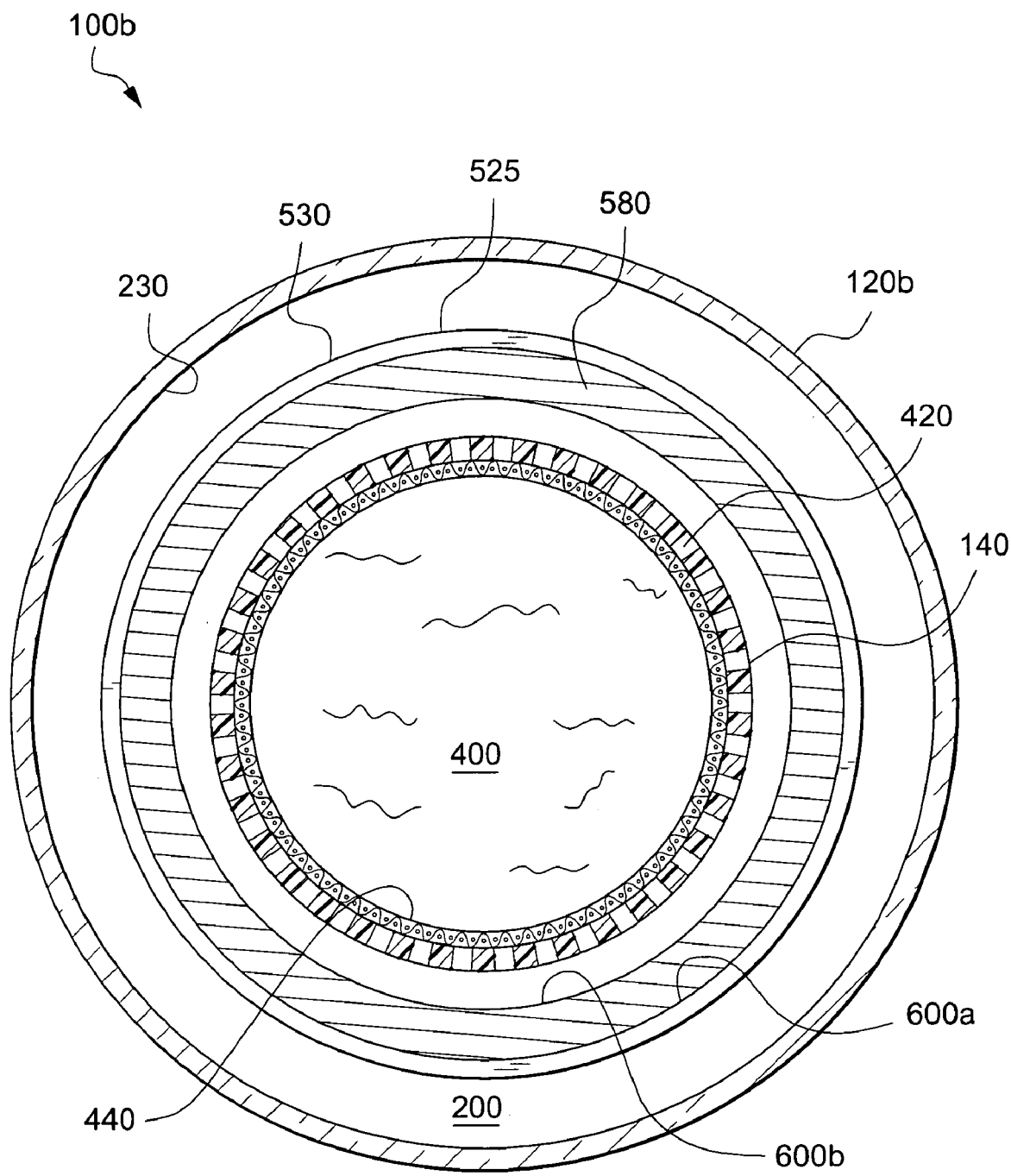
FIG. 10 is a section view taken along lines $10^{-10}$ of the co-culture apparatus of FIG. 9.

FIGS. 9 and 10 show a further embodiment of the present invention. Specifically, a co-culture apparatus 100 (represented by the alpha-numeric label "100b") comprises an exterior receptacle 120b of overall cylindrical shape and lacking neck 240. A screw-cap lid 620b screws onto first end 160 thereby sealing the co-culture apparatus 100b. Cartridge 140 is inserted through comparatively wide aperture 270 and attached to cartridge-mounting member 300. The co-culture apparatus 100b includes optional sleeve 580.

The first cell line is typically a population of progenitor cells such as a cell population of cardiomyocytes derived from adult stem cells. Throughout the following description the term "second cell line" refers to the population of cells in the cartridge 140, and other cell lines (such as the first, third, fourth, fifth and so on) represent designated cell lines in the first chamber 200. As described below, if additional cell lines are used in the first chamber 200, additional first chambers are inoculated with either fresh support cells or a transformation cell population to proliferate or transform the second cell line into a desired target cell line such as cardiomyocytes for repairing, e.g., damaged heart tissue.

During the co-incubation, the cells in the first chamber 200 are in chemical communication with the progenitor cell line in the second chamber 400 of cartridge 140; for convenience the cell line in the second chamber 400 is referred to as the "second cell line". There is preferably no physical contact between the second cell line in the second chamber 400 and the support or transformation cell line in the first chamber 200; should physical contact occur the amount of contact should not amount to co-mingling of the cell lines.

The exterior receptacle 120, cartridge 140, and sleeve 580 may be supplied, for example, in sterile form sealed in: (1) separate sealed bags, the separate bags and their contents previously sterilized using a suitable form and amount of ionizing radiation such as intense gamma rays; (2) the same bag but contained therein as separate items and sterilized in place using, e.g., gamma rays, i.e. the cartridge 140 is not inserted into the exterior receptacle 120; (3) the same bag, wherein the sleeve 580 is already placed inside the exterior receptacle 120, and more specifically with the bottom end 380 attached to the cartridge-mounting member device 300, and sterilized in place using, e.g., gamma rays.

The terms "first cell line" and "first cell population" are regarded as equivalent terms. The terms "second cell line" and "second cell population" are regarded as equivalent terms.

It should be understood that while the second cell population/line normally includes progenitor cells (i.e., cells to be transformed to the target cell population and which are normally inoculated into the cartridge 140), this does not mean the second cell line consists entirely of specific cell lines, but may also include additional groups of cells derived from one or more cell types. Likewise, it should be understood that while the second cell population/line normally includes transformation cells (i.e., cells used to transform the progenitor cells of the first cell line into useful target cells for treating a patient).

EXAMPLES

The invention is further described in the following examples; it is to be understood that the present invention is not limited to the examples described below. Example 1 describes how the method and apparatus of the invention can be applied to selected adult stem cells to derive cardiomyocytes. Example 2 also describes how the method and apparatus of the invention can be utilized to support and transform selected embryonic stem cell line into cardiomyocytes. Additional examples are used to further describe the present invention. It is to be appreciated, however, that these method examples are merely examples of possible co-culture techniques and numerous other techniques or modifications thereof may also be used.

METHOD EXAMPLE 1

Method for Transforming a Stem Cell Population into Cardiomyocytes

In this example the co-culture apparatus according to the invention includes a sleeve constructed of mesh coated with collagen.

Separate cell populations of autologous adult stem cells (progenitor cell line) and support cells are obtained from the same patient. Standard tissue culture methods are used to prepare and process both cell populations. Briefly, a patient's bone marrow is aspirated from multiple sites on the posterior iliac crest. Bone marrow samples are collected in heparinized tubes and resuspended in RPMI-1640 previously conditioned with 10% fetal bovine serum, 1% heparinized autologous plasma and supplemented with hydrocortisone, fungizone, and streptomycin. Cell clumps are disaggregated and divided into aliquots of $2 \times 10^6$ to $5 \times 10^6$ nucleated cells/ml.

Adult stem cells are obtained from the patient's bone marrow and separated over a Ficoll Hypaque (Pharmacia) gradient. The bone marrow suspension is centrifuged at about 3,000 to 3,500 g for about 20 minutes to obtain a buffy coat layer; the buffy coat layer can be removed and used to provide stromal cells). The stem cell fraction is further separated by CD 34+38—by the magnetic cell separation method (MACS system, Miltenyi Biotec. Auburn, Calif.). Selective CD 34+38 stem cells are frozen and stored in 10% glycerol and 10% albumin; alternatively, the stem cells are suspended in proliferation medium and used immediately thereafter.

Stromal cells derived from the Ficoll buffy coat and cultured in the presence of a collagen coated substrate on which at least some of the stromal cells should adhere and form a monolayer; non-adherent stromal cells are continuously removed from the culture. The monolayer of confluent stromal cells are collagenase treated and suspended in proliferation media (PM), which is used to inoculate a sleeve 580 already placed aseptically inside co-culture apparatus 100, and more specifically inside the exterior receptacle 120, which at this point does not contain a cartridge 140. PM comprises Dulbecco's Modified Eagles Medium (DMEM) enriched with 10% human serum, L-glutamine (100×), 1 mM sodium pyruvate, hydrocortisone hemisuccinate and suitable antibiotic. The exterior receptacle 120 containing the inoculated sleeve is placed on a roller deck and rotated at low speed (about 5 to about 20 revolutions per hour).

Once the stromal support cells (for expediency referred to here as "the first cell line") reach semi confluence on the sleeve insert, the PM media is removed from the exterior receptacle 120 and a sterile cartridge 140 is aseptically inserted into the first chamber 200 and attached to the cartridge-mounting member 300. 5–10 ml of 37° C. patient's plasma is added to the second chamber 400 inside cartridge 140. Care is taken to ensure that the plasma is washed over inner-surface 440 of the cartridge 140; excess plasma is removed from the cartridge 140. PM containing Dulbecco's Modified Eagles media (DMEM) enriched with 5–10% human serum, hydrocortisone hemisuccinate is added to the second chamber 400 in sufficient amount to ensure adequate submersion of the cartridge 140, antibiotics are also added to the second chamber 400.

A stem cell population (progenitor or second cell line) is added to the second chamber 400 inside cartridge 140. More specifically, the second chamber 400 is inoculated with a purified stem cell population (CD 34+38) and the co-culture apparatus 100 sealed with by attaching screw cap 620 over neck opening 260.

The co-culture apparatus 100 is placed on a mechanical roller deck initially set at a relatively slow rotation speed (10–20 revolutions per hour (rph)) for the first 24 hours and then increased to 40–60 rph thereafter. The co-culture apparatus 100 is maintained in appropriate environmental conditions at 37° +/−2° C. for 7–10 days on the roller deck. During the 7–10 day incubation period, the stem cells inside the cartridge 140 proliferate with minimal differentiation.

At the end of the 7–10 day incubation period, the cartridge 140 is removed and aseptically submerged in a sterile vessel and washed three times with isotonic phosphate buffered saline (PBS). The cartridge 140, and more particularly the substantially undifferentiated stem cells therein (the second cell line), are now co-cultured with a population of transformation cells (third cell line) to complete the transformation (differentiation) of the second cell line (progenitor cells) into cardiomyocytes.

Human skeletal muscle myoblasts are utilized as the third cell line (the transformation cell line). Homologous myoblasts are isolated and expanded in culture using skeletal muscle media-SkGM-2 (Cambrex) or equivalent media that contains dexamethasone. Specifically, the patient's leg muscle tissue is biopsied and the tissue sample is dissociated with Hepes buffered saline solution and trypsin/EDTA solution. Following neutralization and washing, the resulting cell suspension is placed in a collagen treated T-25 $cm^2$ flasks and covered with Bulletkits (Cambrex) media. The culture is maintained at 37° C.+/−2° C. with 5% $CO_2$ to stimulate an adherent primary myoblast culture. When the primary myoblasts culture is 60 to 90% confluent, the cells are washed, trypsinized, neutralized, and sequentially expanded on increasingly larger pre-coated collagen surfaces from T-25 $cm^2$, to T-75 $cm^2$, to T-225 $cm^2$ flasks. When the myoblasts have reached 60–90% confluence in the T-225 $cm^2$ flasks, the myoblasts are used to inoculate a pre-collagen coated fresh sleeve 580 located inside a fresh exterior receptacle 120 (850 $cm^2$) at a 1:1 ratio. The exterior receptacle 120 is placed on a roller deck and rotated slowly at 10 to 20 rph for the first 24 hours to facilitate the myoblasts in attaching to the sleeve 580. After 24 hours, fresh myoblast media is changed and the rph is increased to about 20– 40 rph. When the myoblasts have reached 30–50% confluency, the proliferated stem cells must be prepared for the differentiation phase of the invention.

Under aseptic conditions, the conditioned media is removed from the exterior receptacle 120 containing the skeletal muscle myoblasts (transformation cell population), and between 1300–1500 ml of Differentiation Medium (DM) containing modified Dulbecco's Modified Eagles Medium (DMEM) (enriched with 5–10% Horse Serum (HS), 5–10% human serum, insulin, isobutylmethylxanine, and dexamethasone, epidermal growth factor), is added to the exterior receptacle 120 containing the skeletal muscle myoblasts. Using the cartridge grip handle 660, the cartridge 140 containing the washed undifferentiated stem cells (second cell line) is aseptically inserted into the exterior receptacle 120 containing the skeletal muscle myoblasts; specifically, cartridge 140 is inserted inside sleeve 580 by attaching the bottom 380 of the cartridge 140 to the cartridge-mounting member 300. The co-culture apparatus 100 is sealed using screw cap 620 and placed on a mechanical roller bottle rotating apparatus set at 50–70 rph and incubated for 14–17 days at 37° C.+/−2° C. at 50% or more relative humidity.

At the end of the 14–17 day incubation period, the adult stem cells derived from bone marrow (second cell line) are transformed into cardiomyocyte aggregates (target cell population) and should express contractile proteins specific to skeletal muscle. The cartridge 140 is aseptically removed from the exterior receptacle 120 and submerged in a sterile container containing 1×PBS and the cardiomyocytes mechanically teased from the interior surfaces of the cartridge 140. The beating cardiomyocyte clusters (target cell line) are placed into a 50 ml centrifuge tube containing 1×PBS and centrifuged at about 1200 rpm for about 5 minutes. The supernatant is removed and the pellet resuspended in a suitable isotonic solution and either used to treat a patient or cryofrozen for later use.

Replenishing the growth medium in both chambers 200 and 400 allows longer co-culture times while maintaining viability of the cell lines in the first and second chambers 200 and 400, respectively.

Thus, the method of transforming a progenitor cell line into a target cell line, comprises the steps of: establishing a progenitor cell line; establishing a support cell line; co-culturing said progenitor and support cell lines; establishing a transformation cell line; and co-culturing said progenitor and transformation cell lines, wherein the transformation cell line supports the transformation of the progenitor cell line into a target cell line.

METHOD EXAMPLE 2

Undifferentiated human embryonic stem cells (second cell line, i.e., progenitor cell population) are prepared as described by Thomson et al. in U.S. Pat. No. 5,843,780. Human blastocysts are obtained in vitro according to Bongso et al., (1989). Human embryos are cultured to the blastocyst state in G1.2 and G2.2 medium according to Gardner et al (1998). Blastocysts are selected for embryonic stem cell isolation. The zona pellucida is removed from the blastocysts by exposure to pronase (Sigma). Inner cell masses are isolated by immunosurgery in which blastocysts are exposed to 1:50 dilution of rabbit anti-human spleen cell antiserum for 30 minutes, then washed for 5 minutes three times in DMEM, and exposed to a 1:5 dilution of Guinea pig complement (Gibco) for 3 minutes, and washed twice in DMEM; lysed trophectoderm cells are removed from the intact inner cell mass (ICM) by gentle pipetting. ICM is either used to inoculate a cartridge 140 and transferred to the co-culture apparatus 100 or cryopreserved for later use.

Human embryonic fibroblast cells (first cell line/support cell line) are derived from human blastocysts as described by Thomason et al. (Science 282, 1145–1147, 1988). Alternatively, human embryonic fibroblast cells are derived from fetal tissue foreskins, wherein foreskin tissue is aseptically placed on a Petri dish and cut into approx. 1 mm$^2$ pieces and later grown to confluence in a T-25 cm$^2$ flask in rich Embryonic Proliferation Medium (EPM). EPM comprises a mixture of Dulbecco's Modified Eagles Medium (DMEM) and Knockout Dulbecco's modified Eagles Medium (KO DMEM) enriched with 20% defined fetal bovine serum, 100× L-glutamine, 1 mM sodium pyruvate, hydrocortisone hemisuccinate, 1% nonessential amino acids, fungizone and antibiotics. Confluent embryonic fibroblast cells are lifted by mild trypsinization and passaged into increasing larger surface area flasks. Once ample embryonic fibroblast cells (2.0–5.0×10$^6$ cells/ml) are cultured they are used to inoculate the collagen coated sleeve 580 already in place inside an exterior receptacle 120 with 175–225 ml of fresh EPM therein, the sleeve 580 is used as a substrate to establish the embryonic fibroblast cells as the support cell line (first cell line). The exterior receptacle 120 is sealed and rotated at about 10–20 rph on a roller bottle rotator; the support cell line adheres to and colonizes the sleeve 580.

After the support cells (first cell line) adhere and grow on the sleeve 580 to greater than 30–50% confluence, the EPM is removed and a sterile cartridge 140 is inserted into the sleeve 580 and attached to the bottom of the exterior receptacle 120. As previously stated, the colonized sleeve 580 has an inner diameter (ID) greater than the outer diameter (OD) of the cartridge 140 and therefore fits around the cartridge 140. Alternatively, the cartridge 140 can be first inserted into the exterior receptacle 120 and the colonized sleeve 580 inserted around the cartridge 140. 5–10 ml of pre-warmed 37° C. patient's serum is added to the inner cartridge. The serum is washed over the inner walls and substrate of the cartridge 140. Excess serum is removed and about a liter of Proliferation Media (PM) is added to the co-culture apparatus 100 containing Dulbecco's Modified Eagles Media (DME); specifically, the PM is added to the exterior receptacle 120 containing the sleeve 580 and cartridge 140. Note: sufficient PM should be added to ensure the cartridge 140 is at least partly submerged particularly when the co-culture apparatus 100 is placed horizontally on a roller bottler-rotating machine. Next, the second cell line is established in the cartridge 140 by inoculating the second chamber 400 inside cartridge 140 with ICM (inner cell mass) (i.e., the second cell line), and sealed with top cap 500. The co-culture apparatus 100 is sealed with screw cap 620 and the apparatus placed on a mechanical roller deck, which is initially set at a relatively slow rotational rate (about 10–20 rph for the first 24 hours and then 40–60 rph thereafter) the first and second cell lines inside the co-culture apparatus are incubated at 37° C.+/−2° C. for 10–14 days on the roller deck.

At the end of the 10–14 day incubation period, the cartridge 140 is removed and aseptically submerged in a sterile vessel and washed three times with isotonic phosphate buffered saline (PBS). The cartridge 140, and more particularly the substantially undifferentiated stem cells therein (the second cell line), are now co-cultured with a population of transformation cells (third cell line) consisting of adult skeletal muscle myoblasts, see next paragraph) to complete the transformation (differentiation) of the second cell line into skeletal muscle myoblast cells.

The third cell line (adult skeletal muscle myoblasts) is prepared and cultured as follows; homologous myoblasts are isolated from and expanded in culture using skeletal muscle media SkGM-2 (Cambrex) or an equivalent media containing dexamethasone. For example, for adult skeletal muscle myoblasts a stimulated patient's leg muscle tissue is biopsied and the tissue sample is dissociated with Hepes Buffered Saline Solution and trypsin/EDTA solution. Following neutralization and washing, the cell suspension is placed in a collagen treated T-25 cm$^2$ flask and covered with Bullekits (Cambrex) media. To stimulate an adherent primary myoblast culture, the culture is maintained at 37° C.+/−2° C. with 5% $CO_2$. Upon 60–90% confluence, the cells are washed, trypsinized, neutralized and sequentially expanded on increasingly larger pre-coated collagen surfaces from T-25, T-75, T-225 flasks. Once the myoblasts have reached 60–90% confluence in the T-225 flask, the myoblasts are then used to inoculate a fresh collagen coated sleeve insert (preferably with an area of 850 cm$^2$ and at a 1:1 ratio) which is placed inside the first chamber 200 of a fresh exterior receptacle 120 to which is added an appropriate amount of support media. The co-culture apparatus 100 is closed using, e.g., screw-cap 620 and placed on a roller deck and rotated at 10–20 rph for the first 24 hours and thence at 20–40 rph. Once the myoblast cells reach 30–50% confluency, they are ready to be used as the third cell line.

Under aseptic conditions, the media in the first chamber containing the sleeve 580 with myoblasts at 30–50% confluency is removed, and between about 1300–1500 ml of differentiation medium (DMEM) containing Dulbecco's Modified Eagles Medium (DMEM); the DMEM contains 5–10% horse serum (HS), 5–10% human serum, insulin, isobutylmethylxanine, and dexamethasone, epidermal growth factor. Using the cartridge grip handle 660, the cartridge 140 containing the washed undifferentiated stem cells (second cell line) is aseptically inserted into the exterior receptacle 120 containing the skeletal muscle myoblasts; specifically, cartridge 140 is inserted inside sleeve 580 by attaching the bottom 380 of the cartridge 140 to the cartridge-mounting member 300. The co-culture apparatus 100 is sealed using screw cap 620 and placed on a mechanical roller bottle rotating apparatus set at 50–70 rph and incubated for 14–17 days at 37° C.+/−2° C. at 50% or more relative humidity.

At the end of the 14–17 day incubation period the adult stem cells (second cell line) are transformed into embryonic cardiomyocytes aggregates (i.e., the target cell line) and should express contractile proteins specific to skeletal muscle. The cartridge 140 is aseptically removed from the exterior receptacle 120 and submerged in a Petri dish containing 1×PBS and the beating embryonic cardiomyocyte clusters are mechanically teased from the interior surfaces of the cartridge 140. The beating embryonic cardiomyocyte clusters are placed into a 50 ml centrifuge tube containing 1×PBS and centrifuged at about 1200 rpm for about 5 minutes. The supernatant is removed and the pellet resuspended as appropriate in isotonic solution and either used to treat a patient or cryofrozen for later use.

METHOD EXAMPLE 3

An exterior receptacle 120 fitted with a sleeve 580 is inoculated with a viable first cell line (support cell line) suspended in a first liquid growth medium; a sufficient amount of the first cell population in the first liquid growth medium is added to the first chamber 200 so that at least portions of the interior surface 230 of first sidewall 220 and the surface 600 of the sleeve 580 are covered by the growth media. The exterior receptacle 120 is sealed and placed horizontally on a roller bottle-rotating machine to establish the support/first cell line. The rotation apparatus is initially rotated at low speed so that the first cell line of support cells attach to both the sleeve 580 and the inner surface 230 of the exterior receptacle 120.

At an appropriate time, the cartridge 140 is used to propagate the second cell line. More specifically, the second chamber 400 is inoculated with a viable second cell line (such as a population of pluripotent stem cells) suspended in a second liquid growth medium. The cartridge 140 is inserted aseptically into the co-culture apparatus 100 and locked in place by mating the bottom end 380 of the cartridge 140 to the sleeve holding member 525; first end 360 of the cartridge 140 sits inside neck 240 and the co-culture apparatus 100 is sealed by attaching screw cap 620 over neck opening 260. The co-culture, apparatus 100 is rotated substantially horizontally on a roller bottle rotator machine.

The second cell line adheres to, and propagates on, the inner-surface 440 of the microporous second sidewall 420 and the hollow fibers 410. Cellular metabolites and cellular products from the first cell line diffuse across the second sidewall 420 to reach the second cell line adhered to the inner-surface 440. Thus, the environment of each cell population is changed by the presence of the other population because cellular metabolites soluble in the aqueous media freely diffuse through the second sidewall 420. The microporous membrane layer 460 functions to keep the cell populations physically separate. The physical separation enables separating harvesting of the first and second cell lines while allowing cellular communication between the cell lines.

The propagation of the second cell line can be interrupted or further transformed by removing the cartridge 140 and placing the same cartridge in a fresh exterior receptacle 120 and thence into a fresh first chamber 200, fitted with or without the sleeve 580, and inoculated with a viable third cell line, which can be the same or different from the first cell line; if different the second cell line is further supported and/or transformed by the third-cell line thereby allowing, for example, a scientist to investigate the impact of various cell lines on the second cell line inside cartridge 140.

At end of a co-incubation, when the first cell line is satisfactorily differentiated and transformed into the desired type of cells, the cartridge 140 is removed from the exterior receptacle 120 (i.e. from the first chamber 200) and the contents of the second chamber 400 are removed (in particular the target cells and hollow fibers 410) and the differentiated cells are mechanically teased and put into suspension. The cellular suspension is centrifuged and supernatant removed, and the pellet is resuspended in fresh isotonic solution (with subsequent washes by further centrifugation and resuspended as appropriate) to provide a final suspension of transformed differentiated cells suitable for therapeutic repair in a patient.

Method example #3 can be summarized: a first cell line (support cell line) is established inside a first receptacle 120 and is used to support the growth of a second cell line inside cartridge 140; the second-cell line is then harvested and used to inoculate a fresh cartridge 140 and co-incubated with a third cell line (the transformation cell line) that transforms the second cell line into the target cell line for use in treating a patient, which may be a human or animal patient.

In addition, as described above, the co-incubation can be manipulated to study the impact of various support and/or transformation cell lines on the second cell line (i.e., the progenitor cell line). For example, a method of transforming a progenitor cell line into a target cell line, comprises the following steps: establishing a progenitor cell line; establishing a support cell line; co-culturing the progenitor and support cell lines; establishing a first transformation cell line; co-culturing the progenitor and first transformation cell lines; establishing a second transformation cell line; and co-culturing the progenitor and second transformation cell lines, wherein the first and second transformation cell lines produce cell metabolites that transform the progenitor cell line.

It is to be understood that the present invention is not limited to the embodiments described above, but encompasses any and all embodiments within the scope of the following claims.

I claim:

1. A co-culture apparatus comprising in combination:
   an exterior receptacle, said exterior receptacle having first and second opposite ends, a first sidewall, said first sidewall having a general cylindrical appearance, said opposite ends and said first sidewall define an internal first chamber, said first sidewall having an internal surface, said second end includes a cartridge-mounting member that faces upward into said first chamber, said first end having an aperture therein, said aperture having an aperture diameter;

a cartridge which fits into said first chamber, said cartridge having first and second opposite ends and a second sidewall between said opposite ends of said cartridge, said cartridge defining a second internal chamber, said second sidewall having an internal surface, wherein said second end of said cartridge mates with said cartridge mounting member, said cartridge having an overall diameter that is less than said aperture diameter, said second sidewall having at least a portion formed from a microporous material;

a sleeve, wherein said sleeve fits inside said first chamber and surrounds said cartridge, wherein said sleeve is attached to said second end of said exterior receptacle; and a closure member that fits over said aperture of said exterior receptacle.

2. The co-culture apparatus of claim 1, wherein said first end of said exterior receptacle includes a neck, and one end of said cartridge rests inside said neck.

3. The co-culture apparatus of claim 1, wherein said sleeve is coated with an extracellular matrix component to improve cell adhesion properties of said sleeve.

4. The co-culture apparatus of claim 1, wherein said sleeve is coated with an extracellular matrix component selected from the group consisting of collagen and fibronectin.

5. The co-culture apparatus of claim 1, wherein said sleeve is attached to said second end of said exterior receptacle by means of a sleeve holding member.

6. The co-culture apparatus of claim 1, wherein said cartridge comprises a column of perforated polymer with a covering of said microporous material to provide said second sidewall.

7. The co-culture apparatus of claim 1, wherein said cartridge comprises a column of perforated polymer with a covering of said microporous material to provide said second sidewall, said second sidewall is secured to said column of perforated polymer by means of top and bottom caps.

8. The co-culture apparatus of claim 1, wherein said cartridge comprises a column of oxygen gas plasma treated polystyrene with a covering of said microporous material to provide said second sidewall, said second sidewall is secured to said column of perforated polymer by means of top and bottom caps.

9. A co-culture apparatus comprising in combination:

an exterior receptacle, said exterior receptacle having first and second opposite ends and a first sidewall, said first sidewall having a general cylindrical appearance, said opposite ends and said first sidewall defining an internal first chamber, said first sidewall having an internal surface, said second end including a cartridge-mounting member that faces upward into said first chamber, said first end having an aperture therein, said aperture having an aperture diameter;

a cartridge which fits into said first chamber, said cartridge having first and second opposite ends and a second sidewall between said opposite ends of said cartridge, said cartridge defining a second internal chamber, said second sidewall having an internal surface, wherein said second end of said cartridge mates with said cartridge mounting member, said cartridge having an overall diameter that is less than said aperture diameter, said second sidewall having at least a portion formed from a microporous material, wherein hollow fibers are located inside said cartridge; and a closure member that fits over said aperture of said exterior receptacle.

10. A co-culture apparatus comprising in combination:

an exterior receptacle, said exterior receptacle having first and second opposite ends and a first sidewall, said first sidewall having a general cylindrical appearance, said opposite ends and said first sidewall define an internal first chamber, said first sidewall having an internal surface, said second end including a cartridge-mounting member that faces upward into said first chamber, said first end having an aperture therein, said aperture having an aperture diameter;

a cartridge which fits into said first chamber, said cartridge having first and second opposite ends and a second sidewall between said opposite ends of said cartridge, said cartridge defining a second internal chamber, said second sidewall having an internal surface, wherein said second end of said cartridge mates with said cartridge mounting member, said cartridge having an overall diameter that is less than said aperture diameter, said second sidewall having at least a portion formed from a microporous material, wherein hollow fibers are located inside said cartridge;

a sleeve, wherein said sleeve fits inside said first chamber and surrounds said cartridge, wherein said sleeve is attached to said second end of said exterior receptacle; and a closure member that fits over said aperture of said exterior receptacle.

* * * * *